United States Patent [19]

Gibbs

[11] 4,164,581
[45] Aug. 14, 1979

[54] 1-(2,6-DICHLOROBENZOYL)-3-(4-TRI-FLUOROMETHYL-2-THIAZOLYL)UREA AND USE AS INSECTICIDE

[75] Inventor: Charles G. Gibbs, Prairie Village, Kans.

[73] Assignee: Gulf Oil Corporation, Pittsburgh, Pa.

[21] Appl. No.: 939,534

[22] Filed: Sep. 5, 1978

[51] Int. Cl.$^2$ .................... A01N 9/12; C07D 277/38
[52] U.S. Cl. ............................ 424/270; 260/306.8 R
[58] Field of Search ................. 260/306.8 R; 424/270

[56] References Cited

U.S. PATENT DOCUMENTS

| 3,748,356 | 7/1973 | Wellinga et al. ................. 260/465 E |
| 3,755,347 | 8/1973 | Guillot et al. ................. 260/306.8 R |

OTHER PUBLICATIONS

Chemical Abstracts, vol. 85, (1976), p. 21468d.

*Primary Examiner*—V. D. Turner
*Attorney, Agent, or Firm*—Carl A. Cline

[57] ABSTRACT

1-(2-Dichlorobenzoyl)-3-(4-trifluoromethyl-2-thiazolyl)urea, which may be made by reacting 2-amino-4-trifluoromethylthiazole with 2,6-dichlorobenzoylisocyanate is highly effective as an insecticide against *Spodoptera efridania* and *Epilachna varivestis*.

5 Claims, No Drawings

1-(2,6-DICHLOROBENZOYL)-3-(4-TRI-FLUOROMETHYL-2-THIAZOLYL)UREA AND USE AS INSECTICIDE

DESCRIPTION OF THE INVENTION

A. Background

1-Halobenzoyl-3-phenylurea compounds have been disclosed to be useful as insecticides, as, for example in U.S. Pat. Nos. 3,450,747 and 3,748,356. 1-Halobenzoyl-3-pyrazinylureas have also been disclosed as insecticides in German Offenlgungsschrift 2,541,116 but the efficacy of the latter compounds is very low. Of the compounds of this type, only diflubenzuron (2,6-difluorobenzoyl 4-chlorophenylurea) has been found to have a combination of properties which makes it commercially interesting. This substance is a potent chitin inhibitor reported to control a wide variety of insect pests. However, one of the metabolism products of this insecticide is 4-chloroaniline, which has been recognized as a carcinogenic substance. Many analogues of diflubenzuron have been made which contain heterocyclic groups instead of the 4-chlorophenyl substituent on the urea structure. Some of these compounds have been shown to be quite effective against the fall armyworm and the housefly. (See De Milo et al, J. Ag and Food Chem. vol. 26 No. 1, pg 164–167(1978)). The dichlorobenzoyl compound which corresponds to diflubenzuron has proved to be excessively toxic, particularly to certain aquatic creatures and to useful insects. The only heterocyclic analogue of this substance which has been reported appears to have inferior insecticidal properties. I have discovered a 2,6-dichlorobenzoylurea, however, which has both desirable efficacy and selectivity, particularly against Mexican bean beetle (*Epilachna varivestis*) and southern armyworm (*Spodoptera efridania*).

B. Statement of the Invention

I have discovered a new insecticidal compound, 1-(2,6-dichlorobenzoyl)-3-(4-trifluoromethyl-2-thiazolyl) urea which possesses unique properties so that it may be used to kill insect pests, particularly southern armyworm and bean beetle larvae by applying an effective amount to infested plants.

PREPARATION OF THE INSECTICIDE

The new insecticide may be prepared by reacting 2-amino-4-trifluoromethylthiazole with 2,6-dichlorobenzoyl isocyanate in an organic solvent reaction medium, as illustrated in the procedure set forth below.

The 4-trifluoromethyl-2-aminothiazole is prepared as taught by J. B. Dickey, et al., *J. Org. Chem.*, 55, 499(1955) and the 2,6-dichlorobenzoylisocyanate is prepared as taught by J. J. Van Daalen, et al., *J. Agr. Food Chem.*, 21, 348(1973).

Preparation of 1-(2,6-dichlorobenzoyl)-3-(4-trifluoromethyl-2-thiazolyl)urea.

To a solution of 1.7 g (0.01 mole) of 4-trifluoromethyl-2-aminothiazole in 50 ml of dry ethylacetate was added all at once to a solution of 2.16 g (0.01 mole) of freshly prepared 2,6-dichlorobenzoylisocyanate dissolved in 10 ml of dry ethylacetate. The mixture was allowed to stir at 25° for 4 hours. The solvent was evaporated in vacuo, ether was added to the residue, and the solid was removed by filtration to give 3.7 g of product, m.p. 210°–213°. The infrared and nuclear magnetic resonance spectra were consistent with the proposed structure.

APPLICATION OF THE INSECTICIDE

It is desirable to apply the insecticide to infested plants as uniformly distributed as possible. Southern armyworm and bean beetle larvae move slowly and feed on the plants, ingesting toxic quantities of the compound. Control will therefore be most effective if the chemical is applied to all areas of the plant, so as to make it available for ingestion. This is best accomplished by means of an aqueous spray of sufficient volume to wet the entire plant, the active agent being contained therein at a relatively low concentration, preferably between 30 and 500 parts per million. A 500 ppm spray mixture may be made by dissolving 25 mg of insecticide in 5 ml of acetone and adding sufficient warm 2 to 3 percent aqueous solution of octylphenoxypolyethoxyethanol emulsifier to make a total volume of 50 ml. Upon shaking, this mixture forms a uniform dispersion, suitable for spraying. Use of the insecticide is illustrated by the following specific example.

EXAMPLE

Bean plants were grown in vermiculite in small paper drinking cups and were sprayed to thorough wetness, each with an aqueous dispersion of the insecticide at a specific concentration. Leaves were removed from the bean plants after spraying and drying and were placed in disposable petri dishes, wherein were also placed 5 southern armyworm larvae (SA) or 5 Mexican bean beetle larvae (MBB). Observations were made on some of the petri dishes each day, as the larvae continued to feed and die. The results were rated according to the following schedule:

0—no larvae dead
1—1 to 25% dead
2—26–50% dead
3—51–75% dead
4—76–99% dead
5—100% dead Observations were recorded after expiration of two days and again after four days. The scores shown in the following table were final scores at the end of four days. The insecticide of the present invention was compared with the corresponding 2,6-difluorobenzoyl compound. Results were as follows:

| Spray Concn. (ppm) | Species | 2,6-Dichlorobenzoyl Compound | 2,6-Difluorobenzoyl Compound |
|---|---|---|---|
| 500 | SA | 5 | 5 |
|  | MBB | 3 | 5 |
| 250 | SA | 5 | 0 |
|  | MBB | 3 | 5 |
| 125 | SA | 5 | 0 |
|  | MBB | 4 | 5 |
| 62 | SA | 5 | 0 |
|  | MBB | 4 | 3 |
| 31 | SA | 5 | 0 |
|  | MBB | 2 | 4 |
| 15 | SA | 5 | 0 |
|  | MBB | 4 | 2 |
| 8 | SA | 5 | — |
|  | MBB | 0 | 0 |

S-614

It may be seen that the corresponding 2,6-difluorobenzoyl compound, or dimilin analogue, is decidedly inferior in activity and is lacking in practical utility for control of southern armyworm.

In the use of the novel insecticide of this invention to control insect larvae it is found that more than one day is usually required for the insect larvae to ingest lethal amounts of insecticide. When plants are sprayed with low concentrations of insecticide, more than three days may be required. At spray concentrations below about 50 ppm it may be advisable to spray more than once so as to insure that sufficient insecticide remains on the plants, available for ingestion by insect larvae. It may also be desirable to repeat sprayings so that new leaves which have grown out between sprayings will receive insecticide. The new insecticide may be formulated by conventional methods, employing solvents, diluents and surface active agents which are commonly available and are approved for agricultural use.

It is understood that an effective amount of chemical is a sufficient amount to achieve a beneficial effect and is usually substantially less than the preferred rate of application, in which the cost of the method is balanced against the increase in value of the crop for maximum overall economic benefit. There may be specific situations in which it is desirable to use considerably more than an effective or a preferred amount of pesticide. An example of such a situation is an integrated pest control program in which many farmers in a very large area are engaged in an effort to substantially eliminate a pest from the entire region. Ordinarily, however, the use of excessive amounts is not economically beneficial.

I claim:

1. The method of killing insect pests on plants which comprises applying to the infested plants an effective amount of 1-(2,6-dichlorobenzoyl)-3-(4-trifluoromethyl-2-thiazolyl)urea.

2. The method according to claim 1 in which the insect pests are southern armyworm larvae.

3. The method according to claim 1 in which the insect pests are Mexican bean beetle larvae.

4. The method according to claim 1 in which the infested plants are sprayed to wetness with an aqueous spray containing from 15 to 500 parts per million of 1-(2,6-dichlorobenzoyl)-3-(4-trifluoromethyl-2-thiazolyl)urea.

5. The insecticidal compound, 1-(2,6-dichlorobenzoyl)-3-(4-trifluoromethyl-2-thiazolyl)urea.

* * * * *